United States Patent [19]

Stockburger

[11] 4,297,290
[45] Oct. 27, 1981

[54] PROCESS FOR PREPARING SORBITAN ESTERS

[75] Inventor: George J. Stockburger, Wilmington, Del.

[73] Assignee: ICI Americas Inc., Wilmington, Del.

[21] Appl. No.: 169,768

[22] Filed: Jul. 17, 1980

[51] Int. Cl.³ .............................................. C09F 5/08
[52] U.S. Cl. ................................. 260/410.6; 536/119
[58] Field of Search ..................................... 260/410.6

[56] References Cited

U.S. PATENT DOCUMENTS

| | | | |
|---|---|---|---|
| 2,322,820 | 6/1943 | Brown | 260/410.6 |
| 2,322,821 | 6/1943 | Brown | 260/410.6 |
| 2,387,842 | 6/1943 | Soltzberg | 260/410.6 |
| 2,390,395 | 12/1945 | Soltzberg | 260/410.6 |
| 4,085,052 | 4/1978 | Murphy et al. | 252/8.4 |

FOREIGN PATENT DOCUMENTS 49-15246 4/1974 Japan .
613444 6/1948 United Kingdom .

OTHER PUBLICATIONS

Brandner, J. D. et al., *Industrial and Engineering Chemistry*, vol. 37, No. 9, pp. 809–812, (1945).

Goldsmith, H. A., *Chemical Reviews*, vol. 33, pp. 257–265, 274, 275, 314–317, and 322–349, (1943).

Kirk–Othmer, "Encyclopedia of Chemical Technology", 2nd Ed., vol. 1, pp. 577–579 & 587, (1963), Published by John Wiley & Sons, Inc., N.Y., N.Y.

MacDonald, I. A., *J. Am. Oil Chemists' Soc.*, vol. 43, pp. 584A, 586A, 616A, 617A and 619A.

Schick, M. J., (Ed.), "Nonionic Surfactants", pp. 247, 248, 264–266, and 294 & 295, (1966), Published by Marcel Dekker, Inc., New York.

Szabo, I. et al., Paper No. 2.44, "Proceedings of the Third Conf. on Applied Chemistry, Unit Operations & Processes", Aug. 29–31, 1977, pp. 487–491, Pub. Magyar Kemikusok Egyesulete, Budapest, Hungary.

*Primary Examiner*—John F. Niebling
*Attorney, Agent, or Firm*—Louis F. Kreek, Jr.

[57] ABSTRACT

Sorbitan fatty acid esters are prepared by forming anhydro sorbitol (a mixture of sorbitans, isosorbide, and unreacted sorbitol) by acid-catalyzed anhydrization, then reacting the resulting anhydro sorbitol with a fatty acid in the presence of a base at a temperature not exceeding about 215° C. Use of temperatures not over 215° C. results in products having substantially less color than those obtained at higher temperatures.

8 Claims, No Drawings

PROCESS FOR PREPARING SORBITAN ESTERS

BACKGROUND OF THE INVENTION

This invention relates to processes for producing sorbitan fatty acid esters.

It is known that sorbitan fatty acid esters can be produced by direct, base-catalyzed reaction of sorbitol with a fatty acid at elevated temperatures. Such process is used commercially and is disclosed, for example, in U.S. Pat. No. 2,322,820 to Brown. Example 3 of this patent describes such reaction at 260° C. Brown also teaches that products containing both hexitan fatty acid esters and hexide esters can be formed in the presence of an acid catalyst, or with no catalyst, stating that acid catalysts tend to produce esters of hexides, while alkaline catalysts tend to produce esters of hexitans. Brown teaches that preferably the hexahydric alcohol and the fatty acid ester are mixed and reacted in the presence of each other from the beginning, although a disclosed alternative is to first treat the hexahydric alcohol to form an inner ether (hexitan or hexide) and thereafter add the fatty acid for esterification.

U.S. Pat. No. 2,322,821 to Brown describes the preparation of hexide esters, either by direct reaction of a hexitol (sorbitol or mannitol) with a fatty acid in the presence of an acid catalyst, or by esterification of a hexide by a reaction with an acid halide (e.g. lauroyl chloride) in a medium made basic with pyridine.

A disadvantage of base catalyzed direct reaction of sorbitol with a fatty acid is that the product is usually highly colored. Treatment with a bleaching agent, such as hydrogen peroxide, sodium hypophosphite, phosphorous acid, or sodium phosphite, is normally required in order to produce a product having commercially acceptable color.

Japanese Patent Publication No. 15246 of 1974 (published Apr. 13, 1974) discloses a process for preparing a sorbitan ester by reaction of sorbitol with a fatty acid, first in the presence of a basic catalyst at 200°–260° C., then in the presence of an acid catalyst at 180°–240° C. According to the publication, esterification takes place mainly during the first portion of the reaction, when a basic catalyst is used, while anhydrization takes place in the presence of the acid catalyst during the second half of the reaction. Patentee claims that sorbitan fatty acid esters produced in his process contain notably less color than those of previous processes such as that described in U.S. Pat. No. 2,322,821. Representative Gardner color values are about 6 or 7; lower color values can be achieved by treating the reaction with a bleaching agent such as hypophosphorous acid.

J. D. Brandner et al., *Industrial and Engineering Chemistry*, vol. 37, no. 9, pages 809–812 (1945) describes esterification of sorbitol with linseed fatty acids, both with and without catalyst, at 180° or 200° C. Calcium acetate and barium acetate are disclosed as catalysts. The products are primarily sorbitol esters, although some anhydrization takes place.

U.S. Pat. No. 2,390,395 to Soltzberg describes the preparation of monoanhydro sorbitol which is rich in 1,4-sorbitan by anhydrization of sorbitol under reduced pressure at 120°–150° C. in the presence of an acid catalyst.

U.S. Pat. No. 2,387,842 to Soltzberg discloses the preparation of "sorbide" (actually a mixture of isomers) by heating sorbitol solution at reduced pressure (88–95 mm of mercury absolute) in the presence of an acid catalyst (sulfuric acid) until 2 moles of water per mole of sorbitol are removed.

The art presently relies on the use of bleaching agents to reduce the color of the products. There is needed a process which will produce sorbitan esters having lower colors than those now obtained when bleaching agents are not used.

SUMMARY OF THE INVENTION

In accordance with the present invention, a sorbitan fatty acid ester is prepared by reacting an anhydro sorbitol containing one or more sorbitans with a fatty acid in the presence of an alkaline catalyst at a temperature not exceeding about 215° C., thereby producing the desired sorbitan fatty acid ester or mixture thereof. The anhydro sorbitol is obtained by heating sorbitol under reduced pressure in the presence of an acid catalyst.

DESCRIPTION OF THE PREFERRED EMBODIMENTS

When preparing a sorbitan ester from sorbitol, it is important in the practice of the present invention to prepare anhydro sorbitol first and then in a separate step to react this anhydro sorbitol with a fatty acid at a temperature not exceeding about 215° C. in the presence of a basic catalyst in order to produce the desired sorbitan fatty acid ester. Applicant has found that it is important to use temperatures not exceeding 215° C. in order to avoid the color formation which has characterized sorbitan esters prepared by prior art methods. It is also essential to carry out anhydrization and esterification as separate steps, rather than as a single step in the manner preferred in the aforesaid U.S. Pat. No. 2,322,820, in order to meet product specifications such as hydroxyl number, acid number, and saponification number without exceeding 215° C.

Esterification of sorbitol at temperatures below 215° C. in the presence of a basic catalyst results in products which do not meet established specifications for sorbitan fatty acid ester surfactants.

Sorbitol is anhydrized in the practice of the present invention until an anhydro sorbitol having the desired degree of anhydrization is obtained. The degree of anhydrization can be determined by measuring the hydroxyl number of a sample according to known techniques. Pure sorbitol, for example, has a hydroxyl number of 1850. An anhydro sorbitol from which an average of 1.0 mole of water has been chemically removed for each mole of sorbitol initially present, has a hydroxyl value of 1368. Broadly, the hydroxyl number of the anhydro sorbitol should be in the range from about 1150 to about 1400, which represents a range from about 1.0 to approximately 1.4, in the degree of anhydrization. More specifically, the desired degree of anhydrization in anhydro sorbitol depends both on the fatty acid and the temperature to be used in esterification. For example, the desired anhydro sorbitol for making a sorbitan monolaurate surfactant has a hydroxyl number in the range of about 1150 to about 1250, while the desired anhydro sorbitol for making a sorbitan monostearate surfactant has a hydroxyl number in the range of about 1250 to about 1400. In each case, an anhydro sorbitol having a hydroxyl value toward the higher end of the range is chosen when an esterification temperature close to 215° C. is to be used, and an anhydro sorbitol having a lower hydroxyl value within the range is chosen when lower esterification temperatures are to be used.

For the present invention, anhydrization is preferably carried out at about 120° C. (although, more broadly, temperatures from about 110° C. to about 150° C. are suitable.) and at reduced pressure (e.g., 5 mm absolute), in the presence of p-toluenesulfonic acid as the acid catalyst, conducting the reaction until a product having the desired hydroxyl number is reached.

It is, of course, understood that other acid catalysts and conditions can be used. It is preferred to carry out anhydrization in the presence of decolorizing carbon.

The degree of anhydrization may be controlled by controlling the reaction time. When anhydrizing sorbitol at 120° C. and at 5 mm of mercury absolute, the reaction time is about 70 minutes when a product having a hydroxyl number of about 1300 is desired, and about 110 minutes when a product having the hydroxyl number of about 1200 is desired. Alternatively the degree of anhydrization may be controlled by choice of reaction temperature, pressure, acid catalyst, catalyst concentration, or a combination of these parameters. An increase in temperature, catalyst concentration, or the strength of the acid catalyst, or a decrease in absolute pressure, increases the degree of anhydrization.

The anhydro sorbitol is a mixture of sorbitans, i.e., 1,4-sorbitan, 2,5-sorbitan, and 3,6-sorbitan, with small amounts of isosorbide and unreacted sorbitol; 1,4-sorbitan is the largest constituent of the anhydro sorbitol.

Anhydro sorbitol, having a hydroxyl number from about 1150 to about 1400 and preferably prepared as described above, is reacted with a fatty acid in the presence of a base at a temperature not exceeding about 215° C. in order to make the desired sorbitan fatty acid ester. The reaction is carried out by heating the anhydro sorbitol, fatty acid, alkaline catalyst, and decolorizing carbon (when used) together, preferably in an inert (e.g., nitrogen) atmosphere until the desired reaction temperature is reached and maintaining this temperature for a sufficient length of time to obtain the desired product. The fatty acid may contain from about 8 to about 22 carbon atoms, although the naturally occuring fatty acids containing from 12 to 18 carbon atoms are preferred. Particularly preferred are lauric, stearic and oleic acids. The fatty acids need not be pure chemical compounds; commerical fatty acid mixtures, such as coconut oil fatty acid, which is a mixture comprising a major amount of lauric acid with smaller amounts of myristic and palmitic acids having an average molecular weight of 201 (and correspondingly an acid number of 279); and commercial stearic acid, consisting essentially of nearly equimolar amounts of palmitic and stearic acids and having an average molecular weight of 271 (and correspondingly an acid number of 207) may be used.

Sodium hydroxide is the preferred alkaline catalyst for esterification, because of its high efficiency and low cost. However, other alkaline materials such as potassium hydroxide, calcium hydroxide, sodium acetate, sodium stearate, or trisodium phosphate, can be used instead of sodium hydroxide if desired.

The amount of fatty acid used is usually in excess of the stoichiometric quantity required for formation of a monoester. The preferred mol ratio of fatty acid to sorbitol varies from about 1.1 when sorbitan monolaurate is being prepared to about 1.33 when sorbitan monostearate is being prepared.

The esterification temperature should not be above about 215° C. as previously noted, because the amount of color formation is undesirably large when higher temperatures are used. On the other hand, the temperature is ordinarily not below about 180° C. because the reaction becomes too slow and esterification may be incomplete at lower temperatures. Temperatures from about 190° C. to about 210° C. are ordinarily preferable. Even within this range, the rate of reaction is noticeably slower and the color of the product noticeably better at 190° than at 210°.

Reaction times from about 2.5 to about 5.0 hours are ordinarily required.

The esterification should be carried out in a substantially anhydrous medium.

The reaction is preferably carried out in the presence of activated carbon which serves as a decolorizing agent.

The reaction is preferably carried out in an inert (e.g., nitrogen) atmosphere.

Best results are obtained by agitating the reaction mixture.

The amount of alkaline catalyst should be limited so that the final product after neutralization will not contain an undesirably large amount of free fatty acid. The amount of sodium hydroxide used will seldom exceed 1% by weight based on the weight of the product. Even smaller amounts are preferred. Preferably the amount of sodium hydroxide used does not exceed the quantity which is chemically equivalent to the maximum quantity of free acid desired in product.

Equivalent quantities of other alkaline materials can be used in place of sodium hydroxide.

When the reaction is completed, reaction may be terminated by cooling the reaction product mixture and adding a small amount of acid, preferably phosphoric acid, sufficient to neutralize the alkali present. Color stability of the product is improved by using at least about one mole of phosphoric acid for every 1.5 moles of sodium hydroxide catalyst used.

The products obtained by the present process are mixtures of sorbitan esters of fatty acids (with some sorbitol amd sorbide esters also present) which are similar to products already known in the art, except that the amount of color associated with the present products is less than the amount of color associated with prior art products which have not been treated with a bleaching agent. This makes it possible to dispense with bleaching treatments, or alternatively to reduce the amount of bleaching agent or to use milder bleaching conditions.

Typical specifications for products of the present invention are as follows:

|  | Sorbitan Mono-laurate | Sorbitan Mono-stearate | Sorbitan Mono-oleate |
| --- | --- | --- | --- |
| Acid No. | 4–7 | 5–10 | 5.5–8 |
| Hydroxyl No. | 330–358 | 235–260 | 149–160 |
| Saponification No. | 158–170 | 145–157 | 193–209 |

The sorbitan monoesters of this invention are useful for the same purposes in general as prior art sorbitan esters.

The sorbitan fatty acid monoesters obtained according to the present invention are useful as wetting agents, surface active agents (surfactants) and emulsifiers. These esters are particularly useful in foods. These esters are water insoluble and oil soluble. These esters are thermally stable and are nontoxic.

The sorbitan fatty acid monoesters obtained according to the present process can be ethoxylated according to procedures known in the art. Ethylene oxide adducts containing an average of about 4 to about 100 or more moles of ethylene oxide per mol of sorbitan monoester can be prepared. The resulting ethylene oxide adducts are known in the art and are useful as hydrophilic surfactants and emulsifiers.

Combinations of sorbitan monoester and the corresponding polyoxyethylene adduct are useful as emulsifying agents, particularly in foods. By appropriate control of the degree of ethoxylation and appropriate choice of the relative amount of sorbitan monoester and its ethoxylated derivative, a wide range of HLB (hydrophlic/lipophilic balance) values and surfactant effects can be achieved.

This invention will now be further described with reference to the specific examples which follow. All percentages are by weight unless otherwise stated.

EXAMPLE 1

Part A. Anhydro sorbitol Intermediate

A solution of commercial sorbitol (1038.6 g., 70% by weight solids containing about 90% sorbitol), and 12.9 g. of decolorizing carbon ("DARCO G-60"), were charged to a 3-neck round bottom flask equipped with a thermocouple, agitator, and a condenser and receiver exiting to a dry ice trap, vacuum gauge, and vacuum pump. The apparatus was evacuated to a pressure of about 5 mm of mercury and the temperature was raised to 90°-95° C. to remove the aqueous solvent. After all the water was removed, 7.2 g. of p-toluenesulfonic acid was charged, the vacuum was again applied, and the charge heated to 120° C. The charge was maintained at this temperature and at 5 mm Hg. pressure for 110 minutes. The charge was then cooled, 1.6 g. of sodium hydroxide and 3.5 g. of diatomaceous earth ("Super-Cel") were added, and the charge was agitated for 15 minutes and filtered under a nitrogen atmosphere at about 90°-110° C. through a sintered glass filter funnel. The product had a hydroxyl number of 1195 (corresponding to a degree of anhydrization of about 1.3) and a Gardner color of 3.

Part B. Sorbitan Monolaurate

Anhydro sorbitol (139.0 g.) prepared in accordance with Part A of this example, commercial lauric acid (181.5 g.), powdered sodium hydroxide (0.764 g.), and decolorizing carbon (4.5 g.) were charged to a 3-neck round bottom flask equipped with a nitrogen inlet, thermocouple, agitator, condenser and receiver exiting to a dry ice trap. The mixture was flushed with nitrogen and heated to 200° C. at atmospheric pressure over a 41 minute period. The reaction mixture was maintained at this temperature and pressure for 360 minutes while a slight nitrogen flow was maintained. The reaction mixture was then cooled and left standing overnight. The next morning the mixture was heated to 101° C. under nitrogen, treated with 1.49 g. of 85% phosphoric acid and 1.5 g. of diatomaceous earth, and filtered through a glass funnel at 90 to 110° C. under nitrogen. A 30 gram sample was withdrawn for color stability test. The remainder was reheated to 100° C. under nitrogen and bleached for 20 minutes with 1.1 g. of 35% aqueous hydrogen peroxide solution. Diatomaceous earth (1.0 g.) was added and the mixture was refiltered.

Analyses of the bleached and unbleached reaction products showed the following:

|  | Unbleached | Bleached |
|---|---|---|
| Acid No. |  | 4.3 |
| Hydroxyl No. |  | 334 |
| Saponification No. |  | 165 |
| Color, (Gardner): |  |  |
| Initial | 4 | 1+ |
| 24 hour | 4 | 1+ |
| 48 hour | 5 | 2 |
| 72 hour | 5 | 4+ |
| 96 hour | 5 | 4+ |

All color values other than initial color were determined by maintaining a product sample at 200° F. (about 93° C.) for the time indicated above.

EXAMPLE 2

Part A. Anhydro Sorbitol Intermediate

The procedure of Example 1, Part A was followed except that anhydrization time was 100 minutes. A product having a hydroxyl number of 1200 was obtained.

Part B. Sorbitan Monolaurate

Anhydro sorbitol (375 g.) prepared in accordance with Part A, 499 g. commercial lauric acid (approximately 51% lauric acid, 18% myristic acid, remainder other fatty acids), 4.5 g. of activated carbon and 2.1 g. of sodium hydroxide were reacted at 200° C. for 360 minutes, following the procedure of Example 1, Part B except as indicated. The product was neutralized with phosphoric acid and filtered through diatomaceous earth, bleached with 0.5% (based on product weight) of 35% (by weight) aqueous hydrogen peroxide solution and again filtered.

Analysis of the product after refiltration showed the following:
Gardner color (initial): less than 1
Acid No.: 4.9
Saponification No.: 162
Hydroxyl No.: 345
Percentage of soap: 0.12

EXAMPLE 3

A. Anhydrization

Deionized sorbitol solution (70% solids) was anhydrized in the manner described in Example 1, Part A, except that the anhydrization time was 70 minutes. A product having a hydroxyl number of 1308 and a Gardner color of 4 was obtained.

Another batch of sorbitol solution was anhydrized in the same manner, yielding a product having a hydroxyl number of 1314 and a Gardner color of 2+.

The two anhydro sorbitol preparations were pooled, giving an anhydro sorbitol having a hydroxyl number of 1311.

B. Esterification

Anhydro sorbitol (324 g.) prepared in accordance with Part A of this example, commercial stearic acid (720.9 g. consisting of approximately 52% by weight stearic acid, 43% by weight palmitic acid, remainder other fatty acids), 2.52 g. powdered sodium hydroxide, and 9.5 g. decolorizing carbon ("DARCO G-60") were charged to the apparatus described in Example 1, Part B. The charge was heated to 200° C. at atmospheric pressure over a period of 57 minutes and maintained at this temperature for 240 minutes. The product was neutralized with 3.9 g. of 85% phosphoric acid, treated with 4.0 g. of diatomaceous earth and filtered. 100 grams of the product was bleached with 0.5% (based on total product weight) of 35% (by weight) aqueous hydrogen peroxide solution at 100° C. and refiltered in the presence of diatomaceous earth (0.5%, based on the total product weight).

The product had the following analysis:
Gardner color (initial): less than 1
Acid No.: 9
Hydroxyl No.: 235
Saponification No.: 151
Percent soap: 0.45

EXAMPLE 4

Part A. Anhydrization

The procedure of Example 3, Part A (second preparation) was used, giving an anhydro sorbitol having a hydroxyl number of 1314.

Part B. Esterification

Anhydro sorbitol (143.4 g.) prepared in accordance with Part A of this example, commercial stearic acid (318.8 g.), sodium hydroxide (1.26 g.), and decolorizing carbon (6.0 g.) were charged to a flask and reacted at 215° C. for 2 hours. The product was treated with 2.50 g. of 85% phosphoric acid and 2.00 g. of diatomaceous earth at 100° C. under nitrogen atmosphere and was filtered. This product had the following properties:
Gardner Color (initial): 4
Gardner Color (92 hours): 5
Acid No.: 13
Saponification No.: 153
Hydroxyl No.: 205

A portion of this product was bleached with 0.5% by weight, based on the product, of 35% aqueous hydrogen peroxide solution at 100° C. for 0.5 hour and refiltered with diatomaceous earth. The refiltered product had an initial Gardner color of 1 and a 92 Gardner Color of 6.

The color of this product is borderline. This illustrates that approximately 215° C. is the maximum reaction temperature for the practice of this invention. The hydroxyl number of the product is below the minimum specification of 235 for sorbitan monostearate. Some polyol anhydrization occurs at this reaction temperature and a higher hydroxyl number anhydro sorbitol is needed to make a product meeting the hydroxyl number specifications.

COMPARATIVE EXAMPLE A

Crystalline sorbitol (128.8 g.) commercial stearic acid (256.4 g.), sodium hydroxide (0.93 g.), and decolorizing carbon (4.03 g.) were charged to an apparatus similar to that described in Example 1. This apparatus was evacuated and charged with nitrogen three times after the reactants were charged and was then heated to 200° C. at atmospheric pressure. The contents of the flask were maintained at 200° C. and atmospheric pressure with a slight nitrogen flow through the flask for 3 hours. The flask contents were cooled to 100° C., neutralized with 5.6 g. of 85% phosphoric acid, treated with diatomaceous earth (3.0 g.) and filtered. The product had the following analysis:
Gardner color (initial): 2
Gardner color (96 hours at 200° F.): 3+
Acid number: 9.7
Saponification No.: 148
Hydroxyl No.: 306
Percent soap: 0.70

The hydroxyl number of this product exceeds the hydroxyl number specification (235-260) for sorbitan monostearate. This example shows that a product meeting the hydroxyl number specification for sorbitan monostearate cannot be made from sorbitol at 200° C., which is the preferred reaction temperature for esterification according to the present invention. Instead, it is necessary to use a higher reaction temperature according to the practice known in the art, which leads to products having an undesirably high Gardner color in the absence of bleaching.

Also, products prepared by esterifying sorbitol with a fatty acid at about 200° C., such as the product of this example, tend to be heterogeneous forming two phases at ambient temperatures. Such products also tend to be difficult to filter, particularly if decolorizing carbon is included in the starting mixture.

What is claimed:

1. A process for preparing a sorbitan fatty acid ester or mixture thereof which comprises reacting an anhydro sorbitol containing a preponderance of sorbitans with a fatty acid in the presence of an alkaline catalyst at a temperature from about 180° to about 215° C., the amount of said catalyst not exceeding the equivalent of about 1% of NaOH, based on product weight, thereby producing said sorbitan fatty acid ester or mixture thereof.

2. A process according to claim 1 in which said alkaline catalyst is sodium hydroxide.

3. A process according to claim 1 in which said anhydro sorbitol is reacted with the said fatty acid at a temperature in the range of about 190° C. to about 210° C.

4. A process for preparing a sorbitan fatty acid ester or mixture thereof which comprises:
  (a) anhydrizing sorbitol in the presence of an acid catalyst to produce an anhydro sorbitol containing a preponderance of sorbitans, and
  (b) reacting said anhydro sorbitol with a fatty acid in the presence of an alkaline catalyst at a temperature from about 180° to about 215° C., the amount of said catalyst not exceeding the equivalent of about 1% of NaOH, based on product weight, thereby producing said sorbitan fatty acid ester or mixture thereof.

5. A process according to claim 4 in which said alkaline catalyst is sodium hydroxide.

6. A process according to claim 4 in which said anhydro sorbitol is heated with said fatty acid at a temperature in the range of about 190° to about 210° C.

7. A process according to claim 1 in which said anhydro sorbitol has a hydroxyl value in the range of about 1150 to about 1400.

8. A process according to claim 4 in which said anhydro sorbitol has a hydroxyl value in the range of about 1150 to about 1400.

* * * * *